United States Patent [19]

Gaussens et al.

[11] 4,196,065

[45] Apr. 1, 1980

[54] HYDROPHOBIC SUBSTRATE WITH GRAFTED HYDROPHILIC INCLUSIONS

[75] Inventors: Gilbert Gaussens, Meudon; Francis Lemaire, Clamart, both of France

[73] Assignee: Commissariat a l'Energie Atomique, Paris, France

[21] Appl. No.: 737,453

[22] Filed: Nov. 1, 1976

Related U.S. Application Data

[63] Continuation of Ser. No. 522,968, Nov. 11, 1974, abandoned.

[30] Foreign Application Priority Data

Nov. 9, 1973 [FR] France .................................. 73 4002

[51] Int. Cl.$^2$ .......................... C08F 2/54; C08F 51/00
[52] U.S. Cl. .......................... 204/159.17; 204/159.15; 204/159.16; 239/34; 239/54
[58] Field of Search ..................... 204/159.15, 159.16, 204/159.17; 260/885

[56] References Cited

U.S. PATENT DOCUMENTS

| | | | |
|---|---|---|---|
| 3,101,275 | 8/1963 | Cairns et al. | 204/159.16 |
| 3,121,672 | 2/1964 | Smith et al. | 204/159.17 |
| 3,247,133 | 4/1966 | Chen | 204/159.15 |
| 3,372,100 | 3/1968 | Charlesby et al. | 204/159.16 |
| 3,607,848 | 9/1971 | Stoy et al. | 204/159.16 |
| 3,826,678 | 7/1974 | Hoffman et al. | 204/159.16 |
| 3,839,172 | 10/1974 | Chapiro et al. | 204/159.17 |
| 3,880,736 | 4/1975 | Garnett et al. | 204/159.12 |
| 3,943,045 | 3/1976 | Cordrey et al. | 204/159.22 |

*Primary Examiner*—Walter C. Danison
*Attorney, Agent, or Firm*—Sughrue, Rothwell, Mion, Zinn and Macpeak

[57] ABSTRACT

A method for the volumetric inclusion and grafting of hydrophilic compounds in a hydrophobic substrate, comprising the steps of immersing said hydrophobic polymerized substrate in a solution containing hydrophilic monomers in the presence of at least one polymerization inhibitor, and irradiating said solution by means of an ionizing radiation, in order to graft and polymerize the hydrophilic inclusions generated by the hydrophilic monomers in said substrate.

56 Claims, 8 Drawing Figures

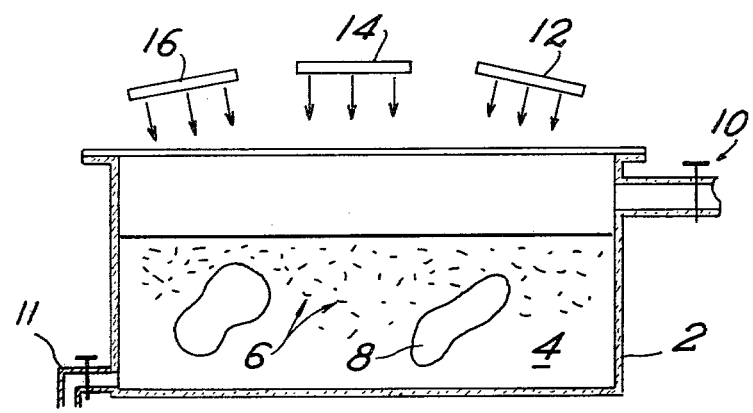
FIG.1
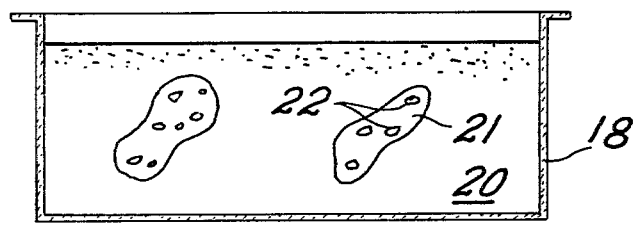
FIG.2
FIG.3
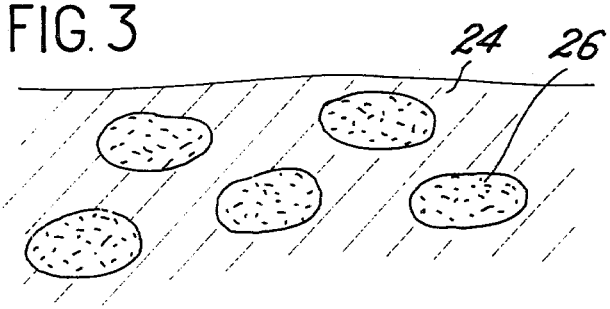

HYDROPHOBIC SUBSTRATE WITH GRAFTED HYDROPHILIC INCLUSIONS

This is a continuation of application Ser. No. 522,968 filed Nov. 11, 1974, now abandoned.

The present invention relates to a method for obtained polymerized hydrophilic inclusions grafted onto hydrophobic substrates, and to the product obtained through said method.

The polymerized hydrophobic substrates onto which are grafted said polymerized hydrophilic inclusions, contingently in a more or less cross-linked state, can be used as such with a view to forming, for instance but not exclusively, diaphragms endowed with selective perviousness.

Moreover, these inclusions can store substances which are soluble in polar medium, e.g. metal salts in aqueous solution. In a number of applications, the hydrophobic substrate with grafted hydrophilic inclusions loaded with soluble substances, is used as a tank of the "sponge type". When in aqueous solution, that tank releases the soluble substances stored in the hydrophilic inclusions.

In fact, it is often quite useful to let metal salts, active constituents (medicaments) or other substances desorb in an aqueous solution, the desorption being carried out at constant velocity and the amount desorbed per unit-time being small. On the other hand, it is sometimes preferable to insert into an inert substrate substances intended to be desorbed in aqueous solution, in order to avoid the drawbacks attached to a direct mechanical contact between the whole mass of active constituents and a human tissue or a solution.

These two conditions have to be met if one wishes to introduce an active medicament uniformly into the human body, or a catalyst or a reaction inhibitor into a solution; in both cases, the catalysts or the active principles must of necessity be stored within an inert substance. Moreover, this inert receptacle should exhibit a controlled perviousness, so as to allow the substances contained therein to migrate, in the presence of water. In addition it is often advantageous that the substance-filled receptacle should not be destroyed in the human body so that it is posible, (provided baryum salts for instance are enclosed therein), to detect its position by radiography.

The invention accordingly relates to a method for the volumetric inclusion of hydrophilic compounds being polymerized and grafted within said substrate.

According to a first embodiment, the method for the volumetric inclusion and grafting of hydrophilic compounds within a hydrophobic substrate into an aqueous or organic solution containing hydrophilic monomers in the presence of at least one polymerization inhibitor, and in irradiating the substrate-filled solution by means of ionizing radiations, with a view to grafting and polymerizing the hydrophilic inclusions obtained from the hydrophilic monomers in the substrate.

In the prior art, e.g. in French Pat. No. 2,104,626, cavities were produced in the hydrophobic substrate prior to inserting hydrophilic polymers, by mixing the hydrophilic inert polymer with a load of powder and stretching it. According to the invention, hydrophobic substrate is submitted to no previous treatment prior to the immersion thereof into the hydrophilic-monomer solution. In order to prevent the hydrophilic monomers from polymerizing in the aqueous solution, at least one polymerization inhibitor is added thereto. The irradiating step aims at polymerizing the hydrophilic monomers and grafting the hydrophilic chains onto the hydrophobic polymers. The ionizing radiation grafts the molecule of an hydrophilic monomer onto the hydrophobic macromolecule, by forming free radicals which lead to the formation of a growing hydrophilic chain thus grafted. The connection between the hydrophilic and hydrophobic chains is a co-valent chemical bond. In the case of hydrocarbonated chains, the bonds are carbon-carbon bonds. Only an ionizing radiation ensures an efficient grafting for fixing the polymerized hydrophilic inclusions in the hydrophobic substrate. Such a grafting proves quite useful for preventing the hydrophilic polymers from leaving the substrate when the latter is put in solution.

According to a second embodiment, the method for the volumetric inclusion and grafting of hydrophilic compounds into a hydrophobic substrate consists in immersing the polymerized hydrophobic substrate into a solution of hydrophilic monomers dissolved in an organic solvent, then extracting the substrate thus impregnated and swollen by said monomer solution, and subsequently irradiating said thus impregnated substrate by means of ionizing radiations, in order to graft and polymerize the hydrophilic inclusions in said substrate.

This second embodiment of the invention dispenses with the polymerization inhibitor in aqueous phase, said inhibitor being likely to constitute a nuisance, whenever the hydrophobic substrate containing inclusions is used for desorbing an active constituent, e.g. in the human body. Indeed, if it has been inserted into the inclusions, the inhibitor may happen to be desorbed together with the substances which, as explained later on, are released by the inclusions, which is itself is prejudicial and sometimes constitutes a definite hindrance, even if the inhibitor is desorbed only in small amounts.

According to this embodiment, the hydrophobic substrate is swollen by the hydrophilic monomer inclusions which penetrate with the help of the solvent, said inclusions not being yet grafted onto the substrate prior to its irradiation by an ionizing radiation. Once the ionizing radiation has been applied, the same product is obtained as with the first embodiment, however without any inhibitor traces in the grafted hydrophilic inclusions.

When hydrophilic monomers in aqueous solution are used, it is also possible, according to a third embodiment of the invention, to introduce into the solution soluble substances stored in the meshes of the hydrophilic inclusion network at the moment of grafting and polymerizing said hydrophilic inclusions by means of ionizing radiation.

According to a fourth embodiment of the invention, to the hydrophilic monomer solution (which is an aqueous solution or a solution of organic solvent) is added a chemical cross-linking agent. This agent is a radically-polymerizing product, such a polyethylene glycol diacrylate, diethylene glycol diacrylate, triethylene glycol diacrylate, tetraethylene glycol diacrylate, polyethylene glycol, dimethacrylate, diethylene glycol methacrylate, triethylene glycol dimethacrylate, tetraethylene glycol dimethacrylate, divinylbenzene, 1-3 butylene glycol dimethacrylate, 1-3 butylene glycol diacrylate, trimethylol propane triacrylate, trimethylol propane trimethacrylate, ethylene diacrylate, ethylene dimethacrylate, 1-6 hexamethylene diacrylate, 1-6 hexamethylene dimethacrylate.

Cross-linking can also be obtained according to a fifth embodiment, after having grafted and polymerized the inclusions, by irradiating the substrate with an ionizing radiation out of the solution, which causes the hydrophilic inclusions to be reticulated.

It is preferable to carry out that operation after having withdrawn the substance from the solution, so as to sever the grafting operations from the reticulation operations. The higher the dose of radiation applied to the substrate provided with inclusions, the more elaborate the reticulation.

Thus, the area of inclusions and, very likely, the size of the meshes of the hydrophilic polymer network, are all the smaller as reticulation is more elaborate. In this way, by regulating the radiation dose, it is possible to control the area of the hydrophilic inclusions as well as the size of the meshes inside the hydrophobic substrate, so as to control the desorption velocity of any products which may be contained in the inclusions by causing the exchange surface of said inclusions to vary. Moreover, in some applications, it is preferable to resort to a cross-linking narrow to the point of hampering the penetration of bacteria through the meshes.

It has been found that the sizes of the grafted zones and the volumetric penetration of inclusions increase according to the increase of the amount of hydrophilic substance polymerized on the same hydrophobic substrate.

The amount of hydrophilic monomers absorbed by the hydrophobic substrate is regulated by regulating the temperature of the hydrophilic monomers solution and/or the immersion duration of the hydrophobic substrates, the concentration of the hydrophilic monomers in solution and/or the dose of ionizing radiation.

The ionizing radiation used can be X-rays, gamma rayon U-V rays or electrom beams.

Preferably use is made of the ionizing rays emitted by artificial or natural radio-elements.

According to a sixth embodiment of the invention, after having obtained the hydrophobic substrate provided with polymerized and grafted hydrophilic inclusions, the dimensions of which are determined by the radiation dose required for cross-linking, one causes substances in aqueous solution to be transferred into the hydrophilic inclusions, by immersing the hydrophilic-inclusion-filled substrate into a solution containing said substances. The latter thus penetrate through the hydrophilic substrate and are stored in the hydrophilic inclusions.

It is not yet very well known how perfusion from the solution water to the hydrophilic inclusions is carried out.

It can be estimated, however, that since some of the hydrophilic inclusions are in the vicinity of the hydrophobic substrate surface, water is allowed to diffuse through the hydrophobic compound polymers, so as to penetrate through the meshes of that polymer and finally reach the hydrophilic inclusion. In the presence of water, these hydrophilic inclusions are caused to swell in the hydrophobic substrate and distend the meshes of the latter, thus promoting assimilation of water by the inclusions in step-by-step fashion.

The hydrophobic substrates treated according to the invention with a view to introducing hydrophilic inclusions, are in a position to store substances dissolved in aqueous solution (in fact, such solutions need not be aqueous, and they simply have to be polar solutions). It has been noticed that inclusions take place in the amorphous areas of the hydrophobic substrate, since the crystalline areas only poorly promote the penetration of hydrophilic substances, because the polymer chains are regularly aligned and the Van der Weels forces between chains are great enough for preventing the hydrophilic inclusions from spacing the chains apart. When the hydrophobic substrate is extracted from the solution containing the substances to be stored in the hydrophilic inclusions, the hydrophobic substrate hydrophilic inclusions do contain said substances, which was ascertained by dipping them in plain water. The regular increase of the concentration of said substances in the water demonstrates that they had previously been stored in the inclusions.

According to the invention, the hydrophobic substrate can be a polymerized thermoplastic organic compound such as vinyl acetate, polyethylene or a copolymwer of vinyl acetate and polyethylene, or, more generally, an ethylene co-polymer, or a polyether, a polyurethane or polyacrylonitrile. It is also possible to use polypropylene, polyamide, polyesters such as ethylene glycol polyterephtalate, polyvinyl chloride, polyformaidehyde chloride, polycarbonates, or also polytetrafluoroethylene ("teflon").

According to the invention, when a chemical cross-linking agent is used, the hydrophilic monomer is ethylene glycol acrylate, ethylene glycol methacrylate, acrylamide, methacrylamide, methylol acrylamide, diacetone acrylamide or an acidic unsaturated substance, such as maleic acid, acrylic acid, methacrylic acid, fumaric acid, itaconic acide, or propylene glycol acrylate or methacrylate.

In more restricted fashion, cross-linking can be achieved by means of ionizing radiations, when the hydrophilic monomer is selected from the group comprising compounds, the carbon of which is not tetrasubstituted, such as acrylamide, ethylene glycol acrylate, methylol acrylamide, diacetone acrylamide, maleic acide, acrylic acid, fumaric acid, itaconic acid and propylene glycol acrylate.

The polymerization inhibitor in the monomer aqueous phase serves to prevent the hydrophilic monomers from polymerizing until the latter is inserted into the hydrophobic substrate. The hydrophilic monomer is polymerized only once it has penetrated into the hydrophobic substrate, polymerization resulting from the ionizing radiations penetrating into the hydrophobic substrate. The polymerization inhibitor is so selected as to prevent the hydrophilic monomer from polymerizing when in solution, while not being efficient enough for preventing polymerization once the hydrophilic monomer has penetrated into the hydrophobic substrate and be submitted to ionizing radiations.

Polymerization and grafting under ionizing radiations can be carried out in the liquid phase, in the monomer solution, provided said solution has been previously degassed.

According to a variant, polymerization can also be carried out in the dry state, after having extracted the impregnated hydrophobic substrate from the aqueous or organic solution.

The invention also radiates to a hydrophobic substrate with polymerized, grafted and more or less cross-linked hydrophilic inclusions.

The very structure of the polymerized hydrophilic inclusions permits to obtain hydrophilic grafted areas, without however impairing the physical and chemical properties of the polymer forming the hydrophobic substrate.

Such inclusions can gather chemical substances, and the latter are slowly released when the substrate is put in the presence of water (or of alcohol).

Other features of the invention will appear from the following description, given merely by way of example, with reference to the accompanying drawing, in which:

FIG. 1 is a diagrammatic view of the device for grafting and polymerizing hydrophilic monomers in a hydrophobic substrate;

FIG. 2 shows the device for storing soluble substances in the hydrophilic inclusions;

FIG. 3 is a cross-section of the hydrophobic substrate with hydrophilic inclusions;

Figure 4:
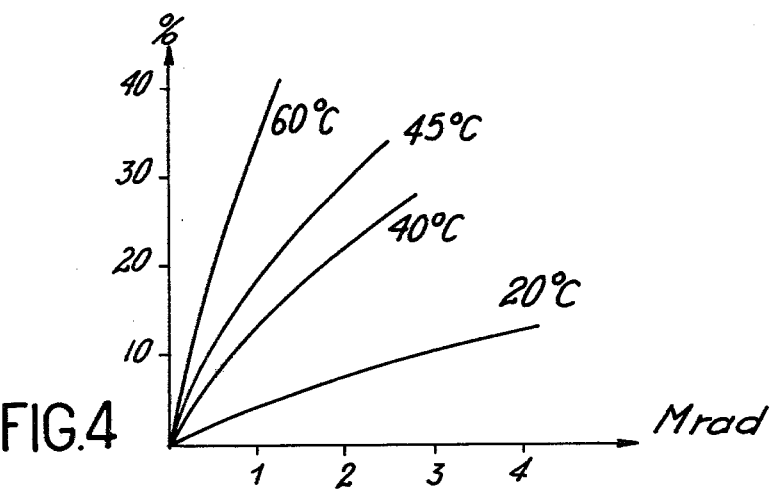
FIG. 4 is a graph plotting the percentage, by weight, of ethylene glycol polyacrylate fixed on a co-polymer of vinyl acetate and of polyethylene, with respect to the radiation dose.

The tank 2, in FIG. 2, contains a solution 4 of hydrophilic monomers 6 in the presence of hydrophobic substrates such as 8.

This tank, or vessel, communicates, through tubing 10, with a pumping device adapted to generate a depressure over the solution with a view to degassing same. Radiation sources 12, 14, 16 direct radiations towards the solution.

According to one embodiment, this device operates as follows: optionally in the presence of a polymerization inhibitor, hydrophilic monomers 6 and the hydrophobic substrates in which said hydrophobic monomers are to be grafted were introduced into aqueous or organic solution 4. The solution was degassed by creating a vacuum is tank 2, and irradiated by means of sources 12, 14 and 16.

Once the hydrophilic monomers were grafted and polymerized, the solution was eliminated by the opening of faucet and the grafted substrates were irradiated again in order to cross-link the hydrophilic inclusions.

Quite obviously, it is also possible to introduce a chemical cross-linking agent into solution 4 and to operate in aqueous solution or in organic solution.

In the case of an organic solution, the hydrophobic substrate is caused to swell when in solution and the ionizing radiations are applied only after having withdrawn the monomer organic solution by opening faucet 11 of tank 2.

It is also possible to introduce into tank 2 soluble products in aqueous solution, intended to be stored in the inclusions. The latter method is valid only provided the substances to be stored are not sensitive to the ionizing radiations.

In FIG. 2 is shown a tank, or vessel, 18 containing a solution 20 (e.g. of metal salts).

The hydrophobic substrate 21 with inclusions 22 of polymerized and grafted hydrophilic substance is placed in that solution. The substances in the solution (e.g. metal salts) perfuse through hydrophobic substrate 21 so as to be stored in the meshes of hydrophilic inclusions 22.

The hydrophobic substrates are then withdrawn and they are ready for serving as "loaded" sponges, since they contain hydrophilic inclusions comprising metal salts.

In FIG. 3 is shown, in cross-section, hydrophobic substrate 24 comprising hydrophilic inclusions such as 26, contingently loaded with soluble substances.

In FIG. 4 are shown graphs plotting the percentage, by weight, of hydrophilic substances (typically ethylene glycol polyacrylate) on polyethylene, with respect to the radiation dose, expressed in Mrads. FIG. 4 indicates that, for the same radiation dose, the percentage, by weight, of ethylene glycol polyacrylate (estimated after drying) increases as temperatures rites.

Thus, for instance, following an irradiation of 1 Mrad, 40%, by weight, of ethylene glycol polyacrylate is fixed on a polyethylene substrate, at the temperature of 60° C.

Figure 5:
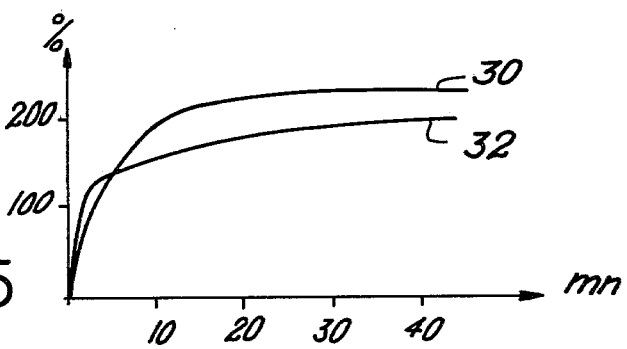
FIG. 5 is a graph plotting the percentage, by weight, of water absorption and alcohol absorption respectively, in ethylene glycol polyacrylate, with respect to time (in minutes) at the temperature of 20° C.

FIG. 5 shows, with respect to time (in minutes), the water-absorption (curve 30) and the alcohol-absorption (curve 32) in polymerized ethylene glycol acrylate. The percentages are by weight. The curves in FIG. 5 relate to the swelling of ethylene glycol polyacrylate, at the temperature of 20° C.

When the ethylene glycol polyacrylate is included in a polymerized substrate, the polyacrylate inclusions store water (or polar substances) in the same manners as mentioned above.

Figure 6:
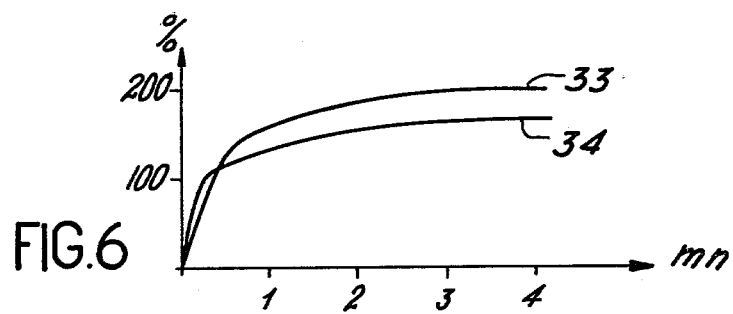
FIG. 6 is similar to FIG. 5, but corresponds to a temperature of 60° C.

FIG. 6 shows with respect to time and the temperature of 60° C., the percentages, by weight, of water-absorption (curve 33) and of alcohol-absorption (curve 34) in ethylene glycol polyacrylate. It is to be noted that, at such temperature (viz 60° C.), ethylene glycol polyacrylate fixes water (together with dissolved salts) much faster, saturation occuring after only a few minutes.

Figure 7:
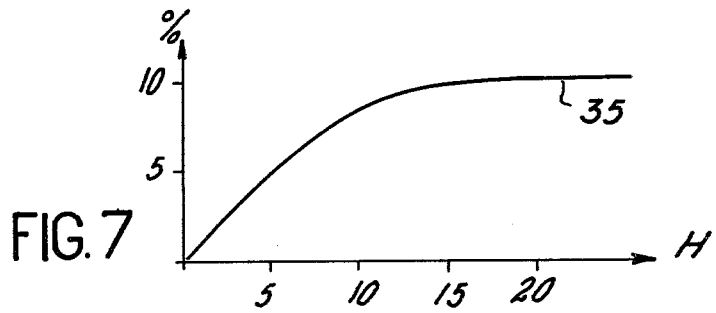
FIG. 7 is a graph plotting the percentage, by weight, of copper-nitrate absorption, with respect to the duration (in hours) of impregnation.

FIG. 7 shows curve 35 plotting, with respect to the duration of impregnation, the percentage of copper-nitrate absorption in polyethylene comprising ethylene glycol polyacrylate inclusions. This percentage is expressed by weight, with respect to the duration (H) of impregnation, expressed in hours.

The curve of FIG. 7 providing the speed of ascention of copper-nitrate in the substrate corresponds to a conversion, or grafting, rate of 22.6%. The percentage of absorbing copper-salt is of course a function of that conversion-rate.

Conversion-rate $\tau$ is given by the expression:

$$\tau = (P - P_0/P_0) \cdot 100$$

wherein $P_0$ is the substrate-weight prior to grafting, and P the substrate-weight after grafting, viz withe hydrophilic inclusions in the hydrophobic substrate.

In FIG. 7, the absorption percentage relates to a 5,000 grams-per-liter nitrate solution, at the temperature of 60° C.

The release of copper ions in solution was examined by submitting the substrate to a flow of isotonic liquid. Experiments have shown that the copper ion loss can be lowered down to amounts as small 20 to 60 micrograms per day.

Hereafter are given the operative parameters:

EXAMPLE 1

The hydrophobic substrate (co-polymer of vinyl acetate and polyethylene) was introduced into a vessel (of the material commercially known as "Pyrex") containing a mixture of 25% ethylene glycol acrylate and 75% water, to which were added 2% copper acetate and 2% copper for inhibiting the monomer homopolymerization. The percentages are given by weight. The vessel content was submitted to a double degassing operation, then to irradiation by a source of $Co^{60}$. In the course of irradiation, the bulb was maintained at the temperature of 45° C. in a thermostated bath.

The dose-rate was 0.2 Mrad per hour, and the dose 1.4 Mrad. Subsequent to irradiation, the substrate was washed, dried and weighed. The conversion-rate was 22.6%. Then was carried out the absorption of copper nitrate by a substrate containing grafted hydrophilic inclusions of ethylene glycol acrylate. The absorption was carried out at 60° C. in a 5000 grams per liter copper-nitrate solution.

The absorption rate with respect to time is given by curve 35 of FIG. 7.

The copper ion release by the loaded substrate submitted to an isotonic-liquid flow-rate of 400 cn.cm per day reached 60 to 20 micro-grams per day.

EXAMPLE 2

According to a second embodiment the method and the hydrophobic substrate were the same as in example 1, the solution introduced into vessel 2 consisting of:

20% ethylene glycol acrylate,

5% diethylene glycol diacrylate (cross-linking agent),

75% methanol, to which were added 1% copper acetate and 0.25% powdered copper (inhibitor). The irradiation temperature was 40° C., the dose-rate 0.1 Mrad per hour and the dose 1.4 Mrad. The conversion-rate was 26% by the absorption velocity of copper-nitrate (the substrate being inversed in a 5000 grams per liter solution) was lower that at example 1, which led to a slower desorption of the same salt.

EXAMPLE 3

According to a third embodiment, the hydrophobic substrate (co-polymer of polyethylene and vinyl acetate) was introduced into a vessel provided with a coolant, containing a solution of three parts of ethylene glycol acrylate, two parts of hexane and five parts of ethanol. The whole was maintained at the temperature of 60° C. in a thermostated bath. Once swollen, the substrate was introduced into a bulb swept with nitrogen, then the whole was submitted to gamma-radiations at room-temperature. The dose-rate was 0.2 Mrad per hour and the total dose 3.4. Mrads.

Figure 8:
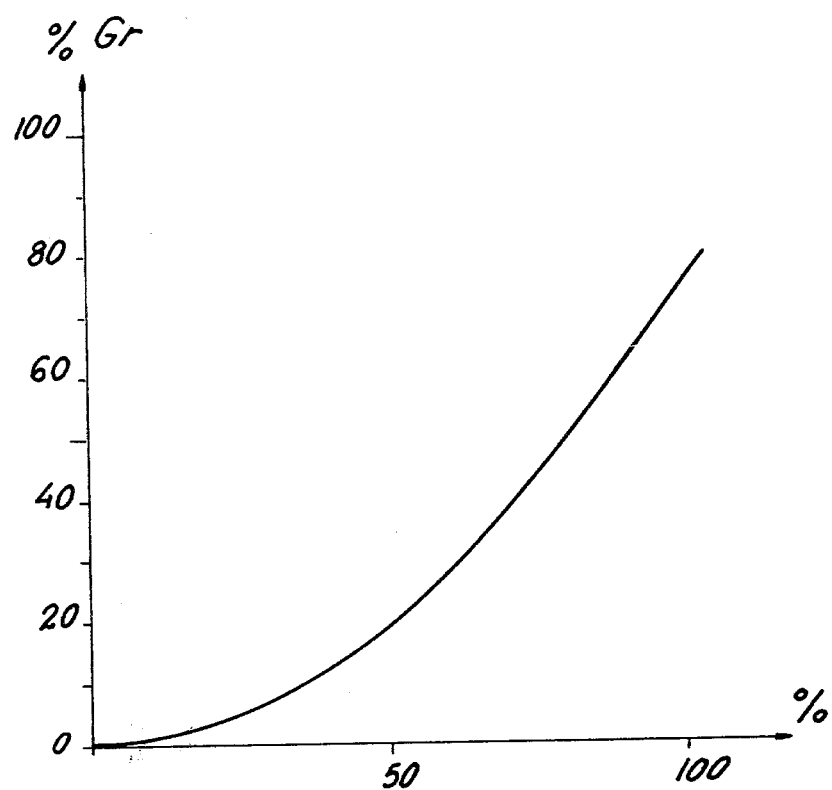
FIG. 8 is a graph plotting the grafting percentage with respect to the swelling percentage, according to a preferred embodiment.

The conversion-rate Gr (% by weight of grafted substance) is a function of the swelling—rate Sw such as shown in FIG. 8 which refers to the present example.

EXAMPLE 4

Substrates grafted according to example 1 were submitted to a nitrogen atmosphere and irradiated with a dose-rate of 0.4 Mrad per hour, to doses of 6.4., 9.6. and 19.2 Mrads.

After 138 hours of copper-nitrate absorption, the weight increase of each substrate was 25%.

The release of the products (copper nitrate) in isotonic solution was definitely greater for the cross-linked substrate irradiated to 6.4 Mrads than for the cross-linked substrates irradiated to 9.6. and 19.2 Mrads, which demonstrates the importance of cross-linking.

EXAMPLE 5

The hydrophobic substrate (viz a co-polymer of vinyl acetate and polyethylene) was introduced into a vessel containing a mixture of 40% ethylene glycol acrylate, 46% water and 10% diethylene glycol diacrylate (cross-linking agent), 2% copper acetate and 2% powdered copper. The operating steps were the same as at example 1, in a 40° C. thermostated bath. The conversion rate was 20% by weight and the absorption rate (viz the percentage, by weight, of copper nitrate stored) reached 11% after immersion of the substrate into a 5000 grams per liter copper-nitrate solution.

EXAMPLE 6

A polyurethane substrate was immersed in a bulb containing a 25% solution of ethylene glycol acrylate in water, to which was added 1% copper acetate and 0.25% powdered copper as inhibitor. Then the whole was degassed twice, at a pressure of $10^{-2}$ torr and irradiated in a 40° C. thermostated bath to a dose of 3.4. Mrads, with a dose-rate of 0.2 Mrad per hour.

The substrate was subsequently washed, dried and weighed. The grafting-rate was 17%.

EXAMPLE 7

Same solution and same substrate (polyurethane) as at example 6.

Irradiation temperature : 60° C.,

Dose-rate: 0.4 Mrad per hour; dose: 6.5 Mrad

Grafting rate: 26.7%.

EXAMPLE 8

A high density polyethylene substrate was immersed in a bulb containing a 50% solution of ethylene glycol and acrylate in methanol, to which was added 1% copper acetate and 0.25% powdered copper, as inhibitor. Then the whole was degassed twice, at a pressure of $10^{-2}$ torr and irradiated in a 60° C. thermostated bath to a dose of 6.5 Mrads, with a dose-rate of 0.4 Mrad per hour. The substrate was subsequently washed, dried and weighed. The grafting-rate was 33%.

EXAMPLE 9

Same operating steps and conditions as at example 8, the substrate being polypropylene.

Grafting rate: 16%.

EXAMPLE 10

Same conditions as at example 8, the substrate being ethylene glycol polyterephtalate.

Grafting rate: 12%.

EXAMPLE 11

Same conditions as at example 8, the substrate being polyvinyl chloride.

Grafting rate: 21%.

EXAMPLE 12

Same conditions as at example 8, the substrate being a copolymer of polyethylene and trifluorochloroethylene.

Grafting rate: 9.5%.

EXAMPLE 13

A polytetrafluoroethylene ("teflon") substrate was immersed in a bulb containing a 50% solution of ethylene glycol acrylate in water, to which were added 1% copper acetate and 0.25% powdered copper, as inhibitor. Then, the whole was degassed twice at a pressure of $10^{-2}$ torr and irradiated in a 60° C. thermostated bath to a dose of 6.5. Mrads, with a dose-rate of 0.4 Mrad per hour.

The substrate was then washed, dried and weighed. Grafting rate 4%.

EXAMPLE 14

Same operating steps as at example 3, with 3% cross-linking agent in the aqueous phase (ethylene glycol diacrylate).

EXAMPLE 15

A polyurethane substrate was immersed in a solution comprising three parts of acrylic acide, two parts of hexane and five parts of ethanol.

That solution is treated as at example 3. With a swelling duration of 24 hours and a total dose of 4 Mrads, the grafting rate was 40%.

EXAMPLE 16

Same operating steps as at example 1, with a low-density polyethylene substrate, 20% acrylic acide, 5% diethyleglycol diacrylate, 73.75% water, 1% copper acetate, and 0.25% powdered copper. The dose rate was 0.145 Mrad per hour, and the dose 1 Mrad. Conversion rate: 13%.

EXAMPLE 17

Copper sulphate was absorbed by a substrate with inclusions dipped in a 1000 grams per liter solution at 60° C. for 20 hours. The substrate weight-increase was 6%.

EXAMPLE 18

Copper, in the nitrate form, was absorbed by the inclusions of a substrate prepared as at example 1 prior to irradiation, by means of a solution, the 75% water of which contained copper nitrate in the proportion of 5000 grams per liter.

The thus formed substrates may contain, in that hydrophilic inclusions, for instance metal salts acting as catalysts in reactions in polar liquide medium (e.g. water).

Thus, a cobalt 2 salt stored in the inclusions and desorbed in solution permits to pass directly to the final product of the reaction of chlorine with a soda solution. The hydrophobic substrate on which the hydrophilic inclusions have been fixed can be in the form of pellets, or of thin diaphragms, or in powdered form.

In the reaction of chlorine with a cold diluted solution of soda in the absence of a catalyst, is obtained a mixture of hypochlorites and chlorides, which, gradually heated, are transformed first into chlorates and chlorides, then into perchlorates and chloride, leading finaly to oxygen+chlorides. Adding a salt of cobalt $2^+$ permits to pass directly from the hypochlorite state to the final step at which oxygen is released.

Similarly, it is possible to store ferrous ions $Fe^{2+}$ in solution in the inclusions, in order to catalyze the oxidation of an iodide $I^-$ to iodine $I_2$ by peroxydisulphate $S_2O_8^{2-}$.

Finally, by way of non limitative examples of commercial applications of the invention, it is possible to store, in the inclusions, the $Mn^{2+}$ ion which catalyzes the reduction of oxalic acids by potassium permanganate in a sulphyric medium, or the $Cu^{2+}$ ion which inhibits the polymerization reactions.

The applications of the product according to the invention are numerous in the medical field. Whenever a soluble medicament must be slowly perfused through the human body, said medicament can be stored in the inclusions. In the human body, the medicament, in contact with water, is dissolved again, and can then cure diseases. More the indestructible pellet can be made impervious to X-rays (e.g. by adding baryum sulphate), thus permitting to locate and control permanently the position of the medicament filled pellet.

It is thus possible to observe the injection of medicaments by radiography.

In view of its flexibility, the hydrophobic substrate (of chemically inert plastic polymer) can be introduced in a number of parts of the human body without any mechanical chafing effect.

What is claimed is:

1. A method for storing polar solvent soluble substance in a solid hydrophobic polymerized substrate and then controllably releasing said substance into a polar solvent, which comprises the steps of:
   (1) storing said substance in said substrate, by
      (a) immersing said solid hydrophobic polymerized substrate in a solution containing ethylenically unsaturated polymerizable hydrophilic monomers in the presence of at least one polymerization inhibitor, a cross linking agent and said polar solvent soluble substance, said polar solvent soluble substance being other than said at least one polymerization inhibitor, said hydrophilic monomers, or said cross linking agent,
      (b) grafting, and polymerizing said hydrophilic monomers in said solid substrate by irradiating said substrate immersed in said solution by means of an ionizing radiation in order to obtain a solid hydrophobic polymerized substrate containing a network of hydrophilic inclusions, and cross-linking said hydrophilic inclusions through said cross-linking agent during said irradiation.
      (c) simultaneously absorbing said polar solvent soluble substance in the hydrophilic inclusions of said substrate while said substrate is immersed in the solution containing said polar solvent soluble substance, and
      (d) removing the substrate containing said substance from said solution; and
   (2) controllably releasing said polar solvent soluble substance from said substrate by contacting said substrate with a polar solvent in order to desorb said substance in said polar solvent at a controlled rate.

2. A method for storing polar solvent soluble substance in a solid hydrophobic polymerized substrate, and then controllably releasing said substance into a polar solvent, which comprises the steps of,
   (1) storing said substance in said substrate, by
      (a) immersing said solid hydrophobic polymerized substrate in a solution containing ethylenically unsaturated polymerizable hydrophilic monomers in the presence of at least one polymerization inhibitor and a cross linking agent, (b) grafting and polymerizing said hydrophilic monomers in said solid substrate by irradiating said substrate immersed in said solution by means of an ionizing radiation in order to obtain a solid hydrophobic polymerized substrate containing a network of hydrophilic inclusions, and cross-linking said hydrophilic inclusions through said cross-linking agent during said irradiation, (c) removing said substrate from said hydrophilic monomer solution, (d) absorbing polar solvent soluble substance in the hydrophilic inclusions of said substrate by dipping said substrate in a solution containing said polar solvent soluble substance, said polar solvent soluble substance being other than said at least one polymerization inhibitor, said hydrophilic monomers or said cross-linking agent, and (e) removing the substrate containing said substance from said solution; and (2) controllably releasing said polar solvent soluble substance from said substrate by contacting said substrate with a polar solvent in order to desorb said substance in said polar solvent at a controlled rate.

3. A method for storing polar solvent soluble substance in a solid hydrophobic polymerized substrate and then controllably releasing said substance into a polar solvent, which comprises the steps of:

(1) storing said substance in said substrate, by (a) immersing said hydrophobic polymerized substrate in a solution of ethylenically unsaturated polymerizable hydrophilic monomers in an organic solvent containing a cross-linking agent to impregnate said substrate by said solution, (b) extracting the thus-impregnated substrate from said solution, (c) grafting and polymerizating said hydrophilic monomers in said solid substrate by irradiating said thus impregnated substrate by means of an ionizing radiation in order to obtain a solid hydrophobic polymerized substrate containing a network of hydrophilic inclusions, and cross-linking said hydrophilic inclusions through said cross-linking agents during said irradiation, (d) absorbing polar solvent soluble substance in the hydrophilic inclusions of said substrate by dipping said substrate in a solution containing said polar solvent soluble substance, said polar solvent soluble substance being other than said cross-linking agents or said hydrophilic monomer, and (e) removing the substrate containing said substance from said solution; and (2) controllably releasing said polar solvent soluble substance from said substrate by contacting said substrate with a polar solvent in order to desorb said substance in said polar solvent at a controlled rate.

4. A method for storing polar solvent soluble substance in a solid hydrophobic polymerized substrate and then controllably releasing said substance into a polar solvent, which comprises the steps of:

1.

(a) immersing said solid hydrophobic polymerized substrate in a solution containing ethylenically unsaturated polymerizable hydrophilic monomers in the presence of at least one polymerization inhibitor and said polar solvent soluble substance, said polar solvent soluble substance being other than said at least one polymerization inhibitor or said hydrophilic monomers, (b) grafting and polymerizing said hydrophilic monomers in said solid substrate by irradiating said substrate immersed in said solution by means of an ionizing radiation in order to obtain a solid hydrophobic polymerized substrate containing a network of hydrophilic inclusions, (c) simultaneously absorbing said polar solvent soluble substance in the hydrophilic inclusions of said substrate while said substrate is immersed in the solution containing said polar solvent soluble substance, (d) removing the substrate containing said substance from said solution, and (e) cross-linking said hydrophilic inclusions by irradiating said substrate by means of ionizing radiation; and (2) controllably releasing said polar solvent soluble substance from said substrate by contacting said substrate with a polar solvent in order to desorb said substance in said polar solvent at a controlled rate.

5. A method for storing polar solvent soluble substance in a solid hydrophobic polymerized substrate, and then controllably releasing said substance into a polar solvent, which comprises the steps of, (1) storing said substance in said substrate, by (a) immersing said solid hydrophobic polymerized substrate in a solution containing ethylenically unsaturated polymerizable hydrophilic monomers in the presence of at least one polymerization inhibitor, (b) grafting and polymerizing said hydrophilic monomers in said solid substrate by irradiating said substrate immersed in said solution by means of an ionizing radiation in order to obtain a solid hydrophobic polymerized substrate containing a network of hydrophilic inclusions, (c) removing said substrate from said hydrophilic monomer solution, (d) cross-linking said hydrophilic inclusions by irradiating said substrate by means of ionizing radiation, (e) absorbing polar solvent soluble substance in the hydrophilic inclusions of said substrate by dipping said substrate in a solution containing said polar solvent soluble substance, said polar solvent soluble substance being other than said at least one polymerization inhibitor or said hydrophilic monomers, and (f) removing the substrate containing said substance from said solution; and (2) controllably releasing said polar solvent soluble substance from said substrate by contacting said substance with a polar solvent in order to desorb said substance in said polar solvent at a controlled rate.

6. A method for storing polar solvent soluble substance in a solid hydrophobic polymerized substrate, and then controllably releasing said substance into a polar solvent, which comprises the steps of, (1) storing said substance in said substrate, by (a) immersing said solid hydrophobic polymerized substrate in a solution containing ethylenically unsaturated polymerizable hydrophilic monomers in the presence of at least one polymerization inhibitor,
(b) grafting and polymerizing said hydrophilic monomers in said solid substrate by irradiating said substrate immersed in said solution by means of an ionizing radiation in order to obtain a solid hydrophobic polymerized substrate containing a network of hydrophilic inclusions,
(c) removing said substrate from said hydrophilic monomer solution,
(d) absorbing polar solvent soluble substance in the hydrophilic inclusions of said substrate by dipping said substrate in a solution containing said polar solvent soluble substance, said polar solvent soluble substance being other than said at least one polymerization inhibitor or said hydrophilic monomers,
(e) removing the substrate containing said substance from said solution, and
(f) cross linking said hydrophilic inclusions by irradiating said substrate by means of ionizing radiation;
(2) controllably releasing said polar solvent soluble substance from said substrate by contacting said substrate with a polar solvent in order to desorb said substance in said polar solvent at a controlled rate.

7. A method for storing polar solvent soluble substance in a solid hydrophobic polymerized substrate and then controllably releasing said substance into a polar solvent, which comprises the steps of:
(1) storing said substance in said substrate, by
(a) immersing said hydrophobic polymerized substrate in a solution by ethylenically polymerizable unsaturated hydrophilic monomers in an organic solvent to impregnate said substrate by said solution,
(b) extracting the thus-impregnated substrate from said monomer solution,
(c) grafting and polymerizing said hydrophilic monomers in said solid substrate by irradiating the thus impregnated substrate by means of an ionizing radiation in order to obtain a solid hydrophobic polymerized substrate containing a network of hydrophilic inclusions,
(d) cross-linking said hydrophilic inclusions by irradiating said substrate by means of ionizing radiation,
(e) absorbing polar solvent soluble substance in the hydrophilic inclusions of said substrate by dipping said substrate in a solution containing said polar solvent soluble substance, said polar solvent soluble substance being other than said hydrophilic monomers, and
(f) removing the substrate containing said substance from said solution; and
(2) controllably releasing said polar solvent soluble substance from said substrate by contacting said substrate with a polar solvent in order to desorb said substance in said polar solvent at a controlled rate.

8. A method for storing polar solvent soluble substance in a solid hydrophobic polymerized substrate and then controllably releasing said substance into a polar solvent, which comprises the steps of:
(1) storing said substance in said substrate, by
(a) immersing said hydrophobic polymerized substrate in a solution of ethylenically unsaturated polymerizable hydrophilic monomers in an organic solvent to impregnate said substrate by said solution,
(b) extracting the thus-impregnated substrate from said monomer solution,
(c) grafting and polymerizing said hydrophilic monomers in said solid substrate by irradiating the thus impregnated substrate by means of an ionizing radiation in order to obtain a solid hydrophobic polymerized substrate containing a network of hydrophilic inclusions,
(d) absorbing polar solvent soluble substance in the hydrophilic inclusions of said substrate by dipping said substrate in a solution containing said polar solvent soluble substances, said polar solvent soluble substance being other than said hydrophilic monomers,
(e) removing the substrate containing said substance from said solution, and
(f) cross linking said hydrophilic inclusions by irradiating said substrate by means of ionizing radiation; and
(2) controllably releasing said polar solvent soluble substance from said substrate by contacting said substrate with a polar solvent in order to desorb said substance in said polar solvent at a controlled rate.

9. A method according to claim 1, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

10. A method according to claim 1, wherein said hydrophobic substrate is selected from the group consisting of polyvinyl acetate, polyethylene, polypropylene, polyamides, polyethyleneterephtalate, polyvinyl chloride, polyformaldehyde chloride, polycarbonates, ethylene co-polymers, polyethers, polyurethanes, polyacronylonitriles, and copolymers of vinyl acetate and ethylene.

11. A method according to claim 1, wherein said hydrophilic monomer is selected from the group consisting of ethylene glycol monoacrylate, ethylene glycol methacrylate, acrylamide, methacrylamide, N-methylol acrylamide, diacetone acrylamide, maleic acid, acrylic acid, methacrylic acid, fumaric acid, itaconic acid, propylene glycol acrylate and propylene glycol methacrylate.

12. The method of claim 1, wherein said hydrophilic monomer is ethylene glycol acrylate.

13. The method of claim 1, wherein said hydrophobic substrate is a thermoplastic organic material.

14. The method according to claim 1, wherein said thermoplastic organic material is a copolymer of vinyl acetate and ethylene.

15. A method according to claim 2, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

16. A method according to claim 2, wherein said hydrophobic substrate is selected from the group consisting of polyvinyl acetate, polyethylene, polypropylene, polyamides, polyethyleneterephtalate, polyvinyl chloride, polyformaldehyde chloride, polycarbonates, ethylene co-polymers, polyethers, polyurethanes, polyacrylonitriles, and copolymers of vinyl acetate and ethylene.

17. A method according to claim 2, wherein said hydrophilic monomer is selected from the group consisting of ethylene glycol monoacrylate, ethylene glycol methacrylate, acrylamide, methacrylamide, N-methylol acrylamide, diacetone acrylamide, maleic acid, acrylic acid, methacrylic acid, fumaric acid, itaconic acid, propylene glycol acrylate and propylene glycol methacrylate.

18. The method of claim 2, wherein said hydrophilic monomer is ethylene glycol acrylate.

19. The method of claim 2, wherein said hydrophobic substrate is a thermoplastic organic material.

20. The method according to claim 2, wherein said thermoplastic organic material is a copolymer of vinyl acetate and ethylene.

21. A method according to claim 3, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

22. A method according to claim 3, wherein said hydrophobic substrate is selected from the group consisting of polyvinyl acetate, polyethylene, polypropylene, polyamides, polyethyleneterephtalate, polyvinyl chloride, polyformaldehyde chloride, polycarbonates, ethylene co-polymers, polyethers, polyurethanes, polyacrylonitriles, and copolymers of vinyl acetate and ethylene.

23. A method according to claim 3, wherein said hydrophilic monomer is selected from the group consisting of ethylene glycol monoacrylate, ethylene glycol methacrylate, acrylamide, methacrylamide, N-methylol acrylamide, diacetone acrylamide, maleic acid, acrylic acid, methacrylic acid, furmaric acid, itaconic acid, propylene glycol acrylate and propylene glycol methacrylate.

24. The method of claim 3, wherein said hydrophilic monomer is ethylene glycol acrylate.

25. The method of claim 3, wherein said hydrophobic substrate is a thermoplastic organic material.

26. The method according to claim 3, wherein said thermoplastic organic material is a copolymer of vinyl acetate and ethylene.

27. A method according to claim 4, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

28. A method according to claim 4, wherein said hydrophobic substrate is selected from the group consisting of polyvinyl acetate, polyethylene, polypropylene, polyamides, polyethylene terephthalate, polyvinyl chloride, polyformaldehyde chloride, polycarbonates, ethylene copolymers, polyethers, polyurethanes, polyacrylonitriles and copolymers of vinyl acetate and ethylene.

29. A method according to claim 4, wherein said hydrophilic monomer is selected from the group consisting of acrylamide, ethylene glycol monoacrylate, N-methylol acrylamide, diacetone acrylamide, maleic acid, acrylic acid, fumaric acid, itaconic acid and propylene glycol acrylate.

30. The method of claim 4, wherein said hydropholic monomer is ethylene glycol acrylate.

31. The method of claim 4, wherein said hydrophobic substrate is a thermoplastic organic material.

32. The method according to claim 4, wherein said thermoplastic organic material is a copolymer of vinyl acetate and ethylene.

33. A method according to claim 5, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

34. A method according to claim 5, wherein said hydrophobic substrate is selected from the group consisting of polyvinyl acetate, polyethylene, polypropylene, polyamides, polyethylene terephthalate, polyvinyl chloride, polyformaldehyde chloride, polycarbonates, ethylene copolymers, polyethers, polyurethanes, polyacrylonitriles and copolymers of vinyl acetate and ethylene.

35. A method according to claim 5, wherein said hydrophilic monomer is selected from the group consisting of acrylamide, ethylene glycol monoacrylate, N-methylol acrylamide, diacetone acrylamide, maleic acid, acrylic acid, fumaric acid, itaconic acid and propylene glycol acrylate.

36. The method of claim 5, wherein said hydrophilic monomer is ethylene glycol acrylate.

37. The method of claim 5, wherein said hydrophobic substrate is a thermoplastic organic material.

38. The method of claim 5, wherein said thermoplastic organic material is a copolymer of vinyl acetate and ethylene.

39. A method according to claim 6, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

40. A method according to claim 6, wherein said hydrophobic substrate is selected from the group consisting of polyvinyl acetate, polyethylene, polypropylene, polyamides, polyethylene terephthalate, polyvinyl chloride, polyformaldehyde chloride, polycarbonates, ethylene copolymers, polyethers, polyurethanes, polyacrylonitriles and copolymers of vinyl acetate and ethylene.

41. A method according to claim 6, wherein said hydrophilic monomer is selected from the group consisting of acrylamide, ethylene glycol monoacrylate, N-methylol acrylamide, diacetone acrylamide, maleic acid, acrylic acid, fumaric acid, itaconic acid and propylene glycol acrylate.

42. The method of claim 6, wherein said hydrophilic monomer is ethylene glycol acrylate.

43. The method of claim 6, wherein said hydrophobic substrate is a thermoplastic organic material.

44. The method according to claim 6, wherein said thermoplastic organic material is a copolymer of vinyl acetate and ethylene.

45. A method according to claim 7, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

46. A method according to claim 7, wherein said hydrophobic substrate is selected from the group consisting of polyvinyl acetate, polyethylene, polypropylene, polyamides, polyethylene terephthalate, polyvinyl chloride, polyformaldehyde chloride, polycarbonates, ethylene copolymers, polyethers, polyurethanes, polyacrylonitriles and copolymers of vinyl acetate and ethylene.

47. A method according to claim 7, wherein said hydrophilic monomer is selected from the group consisting of acrylamide, ethylene glycol monoacrylate, N-methylol acrylamide, diacetone acrylamide, maleic acid, acrylic acid, fumaric acid, itaconic acid and propylene glycol acrylate.

48. The method of claim 7, wherein said hydrophilic monomer is ethylene glycol acrylate.

49. The method of claim 7, wherein said hydrophobic substrate is a thermoplastic organic material.

50. The method according to claim 7, wherein said thermoplastic organic material is a copolymer of vinyl acetate and ethylene.

51. A method according to claim 8, wherein the amount of hydrophilic inclusions formed in said hydrophobic substrate is regulated by regulating the temperature of said hydrophilic monomer solution, the duration of immersion of said hydrophobic substrate, the hydrophilic monomer concentration of said solution and the duration of irradiation.

52. A method according to claim 8, wherein said hydrophobic substrate is selected from the group consisting of polyvinyl acetate, polyethylene, polypropylene, polyamides, polyethylene terephthalate, polyvinyl chloride, polyformaldehyde chloride, polycarbonates, ethylene copolymers, polyethers, polyurethanes, polyacrylonitriles and copolymers of vinyl acetate and ethylene.

53. A method according to claim 8, wherein said hydrophilic monomer is selected from the group consisting of acrylamide, ethylene glycol monoacrylate, N-methylol acrylamide, diacetone acrylamide, maleic acid, acrylic acid, fumaric acid, itaconic acid and propylene glycol acrylate.

54. The method of claim 8, wherein said hydrophilic monomer is ethylene glycol acrylate.

55. The method of claim 8, wherein said hydrophobic substrate is a thermoplastic organic material.

56. The method according to claim 8, wherein said thermoplastic organic material is a copolymer of vinyl acetate and ethylene.

* * * * *